(12) United States Patent
Fisher et al.

(10) Patent No.: US 8,133,261 B2
(45) Date of Patent: Mar. 13, 2012

(54) INTRA-FACET FIXATION DEVICE AND METHOD OF USE

(75) Inventors: Michael Alan Fisher, Middleborough, MA (US); Hassan A. Serhan, South Easton, MA (US); Michael J. O'Neil, West Barnstable, MA (US)

(73) Assignee: DePuy Spine, Inc., Raynham, MA (US)

( * ) Notice: Subject to any disclaimer, the term of this patent is extended or adjusted under 35 U.S.C. 154(b) by 855 days.

(21) Appl. No.: 11/843,132

(22) Filed: Aug. 22, 2007

(65) Prior Publication Data

US 2008/0234758 A1 Sep. 25, 2008

Related U.S. Application Data

(60) Provisional application No. 60/891,616, filed on Feb. 26, 2007.

(51) Int. Cl.
*A61B 17/70* (2006.01)
(52) U.S. Cl. ..................................................... 606/247
(58) Field of Classification Search .................. 606/247, 606/908, 86 R, 76, 301, 286, 328, 312, 916; 411/411, 416
See application file for complete search history.

(56) References Cited

U.S. PATENT DOCUMENTS

| | | |
|---|---|---|
| 3,934,444 A | 1/1976 | Simons |
| 4,011,602 A | 3/1977 | Rybicki et al. |
| 4,263,904 A | 4/1981 | Judet et al. |
| 4,576,534 A * | 3/1986 | Barth et al. ................. 411/412 |
| 4,590,928 A | 5/1986 | Hunt et al. |
| 4,858,603 A | 8/1989 | Clemow et al. |
| 4,878,794 A | 11/1989 | Potucek |
| 4,898,186 A | 2/1990 | Ikada et al. |
| 4,927,421 A | 5/1990 | Goble et al. |
| 4,961,740 A | 10/1990 | Ray et al. |
| 4,988,351 A | 1/1991 | Paulos et al. |
| 5,059,193 A | 10/1991 | Kuslich |
| 5,100,405 A | 3/1992 | McLaren |
| 5,129,904 A | 7/1992 | Illi |
| 5,152,303 A | 10/1992 | Allen |

(Continued)

FOREIGN PATENT DOCUMENTS

EP 0502698 9/1992

(Continued)

OTHER PUBLICATIONS

International Search Report and Written Opinion dated Jul. 25, 2008 for PCT/US08/50194.

(Continued)

*Primary Examiner* — Eduardo C Robert
*Assistant Examiner* — Summer Kostelnik
(74) *Attorney, Agent, or Firm* — Nutter McClennen & Fish LLP (57) ABSTRACT

A implantable interference device configured for intra-facet placement within a facet joint is provided. The device includes a shank capable of engaging opposing faces of the facet joint. The shank can further include a head extending from a proximal end of the shank wherein the head is configured to engage and/or buttress opposing faces of the joint, and also configured for preventing over-insertion of the device. Optionally, at least a portion of the shank can include or be formed of a fusion-promoting bioactive material. Further, a method for providing fixation of a facet joint by intra-facet placement of an interference device within the facet joint is provided.

21 Claims, 10 Drawing Sheets

U.S. PATENT DOCUMENTS

| | | |
|---|---|---|
| 5,156,616 A | 10/1992 | Meadows et al. |
| 5,169,400 A | 12/1992 | Muhling et al. |
| 5,180,388 A | 1/1993 | DiCarlo |
| 5,275,601 A | 1/1994 | Gogolewski et al. |
| 5,314,427 A | 5/1994 | Goble et al. |
| 5,364,400 A | 11/1994 | Rego, Jr. et al. |
| 5,403,136 A | 4/1995 | Mathys et al. |
| 5,409,486 A | 4/1995 | Reese |
| 5,443,509 A | 8/1995 | Boucher et al. |
| 5,456,685 A * | 10/1995 | Huebner ............ 606/321 |
| 5,470,334 A | 11/1995 | Ross et al. |
| D368,777 S | 4/1996 | Goble et al. |
| 5,527,312 A | 6/1996 | Ray |
| 5,545,163 A | 8/1996 | Miller et al. |
| 5,558,674 A | 9/1996 | Heggeness et al. |
| D374,286 S | 10/1996 | Goble et al. |
| D374,287 S | 10/1996 | Goble et al. |
| D374,482 S | 10/1996 | Goble et al. |
| 5,562,672 A | 10/1996 | Huebner et al. |
| 5,571,104 A | 11/1996 | Li |
| 5,571,139 A | 11/1996 | Jenkins, Jr. |
| 5,613,968 A | 3/1997 | Lin |
| 5,645,547 A | 7/1997 | Coleman |
| 5,697,929 A | 12/1997 | Mellinger |
| 5,743,912 A | 4/1998 | Lahille et al. |
| 5,743,914 A * | 4/1998 | Skiba ............ 606/304 |
| 5,840,078 A | 11/1998 | Yerys |
| 5,871,486 A | 2/1999 | Huebner et al. |
| 5,885,300 A | 3/1999 | Tokuhashi et al. |
| 5,888,228 A | 3/1999 | Knothe et al. |
| 5,925,047 A | 7/1999 | Errico et al. |
| 5,947,969 A | 9/1999 | Errico et al. |
| 5,951,560 A | 9/1999 | Simon et al. |
| 5,964,761 A | 10/1999 | Kambin |
| 5,968,047 A | 10/1999 | Reed |
| 5,989,255 A | 11/1999 | Pepper et al. |
| 6,007,539 A * | 12/1999 | Kirsch et al. ............ 606/75 |
| 6,030,162 A | 2/2000 | Huebner |
| 6,045,554 A | 4/2000 | Grooms et al. |
| 6,048,343 A | 4/2000 | Mathis et al. |
| 6,080,157 A | 6/2000 | Cathro et al. |
| 6,096,060 A | 8/2000 | Fitts et al. |
| 6,099,529 A | 8/2000 | Gertzman et al. |
| 6,126,663 A | 10/2000 | Hair |
| 6,162,225 A | 12/2000 | Gertzman et al. |
| 6,214,007 B1 | 4/2001 | Anderson |
| 6,214,012 B1 | 4/2001 | Karpman et al. |
| 6,277,149 B1 | 8/2001 | Boyle et al. |
| 6,283,973 B1 | 9/2001 | Hubbard et al. |
| 6,383,187 B2 | 5/2002 | Tormala et al. |
| 6,402,757 B1 | 6/2002 | Moore, III et al. |
| 6,461,373 B2 | 10/2002 | Wyman et al. |
| 6,464,706 B1 | 10/2002 | Winters |
| 6,485,518 B1 | 11/2002 | Cornwall et al. |
| 6,488,683 B2 | 12/2002 | Lieberman |
| 6,506,192 B1 | 1/2003 | Gertzman et al. |
| 6,527,773 B1 | 3/2003 | Lin et al. |
| 6,540,747 B1 | 4/2003 | Marino |
| 6,565,572 B2 | 5/2003 | Chappius |
| 6,569,186 B1 | 5/2003 | Winters et al. |
| 6,575,976 B2 * | 6/2003 | Grafton ............ 606/916 |
| 6,585,518 B1 | 7/2003 | Jenkins et al. |
| 6,589,245 B1 * | 7/2003 | Weiler et al. ............ 623/13.14 |
| 6,629,977 B1 | 10/2003 | Wolf |
| 6,641,583 B2 | 11/2003 | Shluzas et al. |
| 6,648,893 B2 | 11/2003 | Dudasik |
| 6,666,868 B2 | 12/2003 | Fallin |
| 6,685,706 B2 | 2/2004 | Padget et al. |
| 6,723,095 B2 | 4/2004 | Hammerslag |
| 6,808,526 B1 | 10/2004 | Magerl et al. |
| 6,811,567 B2 | 11/2004 | Reiley |
| 6,921,402 B2 | 7/2005 | Contiliano et al. |
| 6,923,814 B1 | 8/2005 | Hildebrand et al. |
| 6,945,975 B2 | 9/2005 | Dalton |
| 6,966,930 B2 | 11/2005 | Arnin et al. |
| 6,976,818 B2 * | 12/2005 | Levey et al. ............ 411/412 |
| 6,979,333 B2 | 12/2005 | Hammerslag |
| 6,981,974 B2 | 1/2006 | Berger |
| 7,056,341 B2 | 6/2006 | Crozet |
| 7,090,675 B2 | 8/2006 | Songer |
| 7,101,398 B2 | 9/2006 | Dooris et al. |
| 7,410,789 B2 | 8/2008 | Schlosser et al. |
| 7,491,221 B2 | 2/2009 | David |
| 7,708,761 B2 | 5/2010 | Peterson |
| 7,799,057 B2 | 9/2010 | Hudgins et al. |
| 7,909,826 B2 | 3/2011 | Serhan et al. |
| 2001/0029375 A1 | 10/2001 | Betz et al. |
| 2002/0042615 A1 | 4/2002 | Graf et al. |
| 2002/0151895 A1 | 10/2002 | Soboleski et al. |
| 2002/0177898 A1 | 11/2002 | Crozet |
| 2002/0183747 A1 | 12/2002 | Jao et al. |
| 2003/0032960 A1 | 2/2003 | Dudasik |
| 2003/0040746 A1 | 2/2003 | Mitchell et al. |
| 2003/0125740 A1 | 7/2003 | Khanna |
| 2003/0153921 A1 | 8/2003 | Stewart et al. |
| 2004/0006342 A1 | 1/2004 | Altarac et al. |
| 2004/0082956 A1 * | 4/2004 | Baldwin et al. ............ 606/73 |
| 2004/0087948 A1 | 5/2004 | Suddaby |
| 2004/0111093 A1 | 6/2004 | Chappuis |
| 2004/0127906 A1 | 7/2004 | Culbert et al. |
| 2004/0127989 A1 | 7/2004 | Dooris et al. |
| 2004/0143267 A1 * | 7/2004 | Fallin ............ 606/73 |
| 2004/0143268 A1 | 7/2004 | Falahee |
| 2004/0167520 A1 | 8/2004 | Zucherman et al. |
| 2004/0186475 A1 | 9/2004 | Falahee |
| 2004/0225292 A1 | 11/2004 | Sasso et al. |
| 2004/0225360 A1 | 11/2004 | Malone |
| 2004/0230192 A1 | 11/2004 | Graf |
| 2004/0249376 A1 | 12/2004 | Hammerslag |
| 2004/0254575 A1 | 12/2004 | Obenchain et al. |
| 2004/0260296 A1 | 12/2004 | Kaiser et al. |
| 2004/0260298 A1 | 12/2004 | Kaiser et al. |
| 2005/0015060 A1 | 1/2005 | Sweeney |
| 2005/0038434 A1 | 2/2005 | Mathews |
| 2005/0113929 A1 | 5/2005 | Cragg et al. |
| 2005/0119657 A1 | 6/2005 | Goldsmith |
| 2005/0124993 A1 | 6/2005 | Chappuis |
| 2005/0149030 A1 | 7/2005 | Serhan et al. |
| 2005/0165399 A1 | 7/2005 | Michelson |
| 2005/0177240 A1 | 8/2005 | Blain |
| 2005/0192572 A1 | 9/2005 | Abdelgany et al. |
| 2005/0197660 A1 | 9/2005 | Haid et al. |
| 2005/0197700 A1 | 9/2005 | Boehm et al. |
| 2005/0216016 A1 | 9/2005 | Contiliano et al. |
| 2005/0222681 A1 | 10/2005 | Richley et al. |
| 2005/0228384 A1 | 10/2005 | Zucherman et al. |
| 2005/0234551 A1 | 10/2005 | Fallin et al. |
| 2005/0234552 A1 | 10/2005 | Reiley |
| 2005/0240188 A1 | 10/2005 | Chow et al. |
| 2005/0251256 A1 | 11/2005 | Reiley |
| 2005/0261770 A1 | 11/2005 | Kuiper et al. |
| 2005/0267480 A1 | 12/2005 | Suddaby |
| 2005/0273110 A1 | 12/2005 | Boehm et al. |
| 2006/0004358 A1 | 1/2006 | Serhan et al. |
| 2006/0004367 A1 | 1/2006 | Alamin et al. |
| 2006/0004448 A1 | 1/2006 | Casey |
| 2006/0004449 A1 | 1/2006 | Goble et al. |
| 2006/0004451 A1 | 1/2006 | Goble et al. |
| 2006/0009847 A1 | 1/2006 | Reiley |
| 2006/0009848 A1 | 1/2006 | Reiley |
| 2006/0015105 A1 | 1/2006 | Warren et al. |
| 2006/0030948 A1 | 2/2006 | Manrique et al. |
| 2006/0036243 A1 | 2/2006 | Sasso et al. |
| 2006/0036323 A1 | 2/2006 | Carl et al. |
| 2006/0041311 A1 | 2/2006 | McLeer |
| 2006/0052785 A1 | 3/2006 | Augostino et al. |
| 2006/0064099 A1 | 3/2006 | Pavlov et al. |
| 2006/0085068 A1 | 4/2006 | Barry |
| 2006/0089646 A1 | 4/2006 | Bonutti |
| 2006/0095036 A1 | 5/2006 | Hammerslag |
| 2006/0095040 A1 | 5/2006 | Schlienger et al. |
| 2006/0106381 A1 | 5/2006 | Ferree et al. |
| 2006/0111179 A1 | 5/2006 | Inamura |
| 2006/0111779 A1 | 5/2006 | Petersen |
| 2006/0111782 A1 | 5/2006 | Petersen |
| 2006/0122609 A1 | 6/2006 | Mirkovic et al. |
| 2006/0149239 A1 | 7/2006 | Winslow et al. |

| | | | |
|---|---|---|---|
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0178743 A1 | 8/2006 | Carter |
| 2006/0190081 A1 | 8/2006 | Kraus et al. |
| 2006/0200137 A1 | 9/2006 | Soboleski et al. |
| 2006/0217714 A1 | 9/2006 | Serhan et al. |
| 2006/0235388 A1 | 10/2006 | Justis et al. |
| 2006/0235391 A1 | 10/2006 | Sutterlin |
| 2006/0241597 A1 | 10/2006 | Mitchell et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0264953 A1 | 11/2006 | Falahee |
| 2006/0271054 A1 | 11/2006 | Sucec et al. |
| 2006/0276790 A1 | 12/2006 | Dawson et al. |
| 2006/0276801 A1 | 12/2006 | Yerby et al. |
| 2006/0293658 A1 | 12/2006 | Sharim |
| 2007/0016191 A1 | 1/2007 | Culbert et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0055236 A1 | 3/2007 | Hudgins et al. |
| 2007/0055373 A1 | 3/2007 | Hudgins et al. |
| 2007/0073290 A1 | 3/2007 | Boehm |
| 2007/0118132 A1 | 5/2007 | Culbert et al. |
| 2007/0135814 A1 | 6/2007 | Farris |
| 2007/0233093 A1 | 10/2007 | Falahee |
| 2007/0250166 A1 | 10/2007 | McKay |
| 2008/0103512 A1 | 5/2008 | Gately |
| 2008/0177334 A1 | 7/2008 | Stinnette |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0275507 A1 | 11/2008 | Triplett et al. |
| 2008/0306537 A1 | 12/2008 | Culbert |
| 2008/0306555 A1 | 12/2008 | Patterson et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012566 A1 | 1/2009 | Fauth |
| 2009/0036926 A1 | 2/2009 | Hestad |
| 2009/0036986 A1 | 2/2009 | Lancial et al. |
| 2009/0099602 A1 | 4/2009 | Aflatoon |
| 2009/0105716 A1 | 4/2009 | Barrus |
| 2009/0125066 A1 | 5/2009 | Kraus et al. |
| 2009/0138053 A1 | 5/2009 | Assell et al. |
| 2009/0192551 A1 | 7/2009 | Cianfrani et al. |
| 2009/0312763 A1 | 12/2009 | Mccormack et al. |

FOREIGN PATENT DOCUMENTS

| | | | |
|---|---|---|---|
| EP | 0856293 A1 | 8/1998 |
| EP | 1210914 A1 | 6/2002 |
| EP | 1248568 A2 | 10/2002 |
| EP | 1452146 A1 | 9/2004 |
| EP | 1585449 A1 | 10/2005 |
| EP | 1813216 A1 | 8/2007 |
| WO | WO-0041636 A1 | 7/2000 |
| WO | 0062684 A1 | 10/2000 |
| WO | WO-0062684 A1 | 10/2000 |
| WO | 0141681 A1 | 6/2001 |
| WO | WO-0141681 | 6/2001 |
| WO | WO-0141681 A1 | 6/2001 |
| WO | 0234120 A2 | 5/2002 |
| WO | WO-03007829 A1 | 1/2003 |
| WO | 2004043278 A1 | 5/2004 |
| WO | 2004100808 A1 | 11/2004 |
| WO | WO-2004110288 A2 | 12/2004 |
| WO | 2005004733 A1 | 1/2005 |
| WO | WO-2005042036 A2 | 5/2005 |
| WO | 2005060845 A1 | 7/2005 |
| WO | 2005076974 A2 | 8/2005 |
| WO | WO-2005097005 A1 | 10/2005 |
| WO | 2006007739 A1 | 1/2006 |
| WO | WO-2006002684 A1 | 1/2006 |
| WO | WO-2006009855 A2 | 1/2006 |
| WO | 2006047707 A2 | 5/2006 |
| WO | 2006057943 A2 | 6/2006 |
| WO | 2006065774 A1 | 6/2006 |
| WO | 2006096241 A2 | 8/2006 |
| WO | 2006096803 A2 | 9/2006 |
| WO | 2006116119 A2 | 11/2006 |
| WO | 2007019710 A1 | 2/2007 |
| WO | 2007041698 A1 | 4/2007 |
| WO | 2007047711 A2 | 4/2007 |
| WO | 2007063399 A1 | 6/2007 |
| WO | 2007075454 A1 | 7/2007 |
| WO | 2007120903 A2 | 10/2007 |
| WO | 2007127610 A1 | 11/2007 |
| WO | 2008124196 A2 | 10/2008 |
| WO | WO-2008153732 A1 | 12/2008 |
| WO | 2009018220 A1 | 2/2009 |
| WO | 2009067486 A2 | 5/2009 |
| WO | WO-2009138053 A1 | 11/2009 |

OTHER PUBLICATIONS

International Search Report and Report Opinion dated Sep. 16, 2008 for PCT/US08/59889.

International Search Report and Written Opinion dated Sep. 24, 2008 for PCT/US08/59866.

Frank M. Phillips, M.D., "Effect of Supplemental Translaminar Facet Screw Fixation on the Stability of Stand-Alone Anterior Lumbar Interbody Fusion Cages Under Physiologic Compressive Preloads", Spine vol. 29, No. 16, pp. 1731-1736, , Lippincott Williams & Wilkins, Inc © 2004, Augus.

Youssef Masharawi, PhD, et al., "Facet Orientation in the Thoracolumbar Spine", Spine vol. 29, No. 16, pp. 1755-1763, © 2004, Lippincott Williams & Wilkins, Inc.

Brian P. Beaubien, BME, et al., "Posterior Augmentation of an Anterior Lumbar Interbody Fusion", Spine vol. 29, No. 19, pp. E406-E412, © 2004, Lippincott Williams & Wilkins, Inc.

Frank Kandziora, M.D., et al., "Biomechanical Testing of the Lumbar Facet Interference Screw", Spine vol. 30, No. 2, pp. E34-E39, © 2005, Lippincott Williams & Wilkins, Inc.

Neil Duggal, M.D., et al., "Unilateral Cervical Facet Dislocation: Biomechanics of Fixation", Spine vol. 30, No. 7, pp. E164-E168, © 2005, Lippincott Williams & Wilkins, Inc.

Youssef masharawi, PhD, BPT, et al., "Facet Tropism and Interfacet Shape in the Thoracolumbar Vertebrae", Spine vol. 30, No. 11, pp. E281-E292, © 2005, Lippincott Williams & Wilkins, Inc., Aug. 15, 2004.

Brian P. Beaubien, BME, et al., "In Vitro, Biomechanical Comparison of an Anterior Lumbar Interdody Fusion with an Anteriorly Placed, Low-Profile Lumbar Plate and Posteriorly Placed Pedicle Screws or Translaminar Screws", Spine vol. 30, No. 16, pp. 1846-1851, © 2005, Lippincott Williams & Wilkins, Inc.

David W. Polly, Jr., M.D., et al. "Surgical Treatment for the Painful Motion Segment", Spine vol. 30, No. 16S, pp. S44-S51, © 2005, Lippincott Williams & Wilkins, Inc.

Douglas Burton, M.D., et al., "Biomechanical Analysis of Posterior Fixation Techniques in a 360° Arthrodesis Model", Spine vol. 30, No. 24, pp. 2765-2771, © 2005, Lippincott Williams & Wilkins, Inc.

Langston T, Holly, M.D., et al., "Percutaneous Placement of Posterior Cervical Screws Using Three-Dimensional Fluoroscopy", Spine vol. 31, No. 5, pp. 536-540, © 2006, Lippincott Williams & Wilkins, Inc.

Frank M. Phillips, M.D., et al., "Radiographic Criteria for Placement of Translaminar Facet Screws", The Spine Journal 4 (2004) 465-467.

Andrew V. Slucky, M.D., et al., "Less Invasive Posterior Fixation Method Following Transforaminal Lumbar Interbody Fusion: a Biomechanical Analysis", The Spine Journal 6 (2006) 78-85.

U.S. Appl. No. 12/834,397 for "Pedicular Facet Fusion Screw With Plate" filed Jul. 12, 2010.

U.S. Appl. No. 12/834,417 for "Pedicular Facet Fusion Screw With Plate" filed Jul. 12, 2010.

Brain W. Su, MD, et al. "An Anatomic and Radiographic Study of Lumbar Facets Relevant to Percutaneous Transfacet Fixation", Spine vol. 34, No. 11, pp. E384-E390, 2009, Lippincott Williams & Wilkins.

Ch. D. Ray, "Transfacet Decompression with Dowel Fixation: a New Technique for Lumbar Lateral Spinal Stenosis", Acta Neurochirurgica, Suppl. 43, 48-54 (1988) © by Springer-Verlag 1988.

Th.-M. Markwalder, et al, "Translaminar Screw Fixation in Lumbar Spine Pathology", Acta Neurochir (Wien) (1989) 99: 58-60.

Matthijs R. Krijnen, M.D., et al, "Does Bioresorbable Cage Material Influence Segment Stability in Spinal Interbody Fusion?" Clinical Orthopaedics and Related Research, No. 448, pp. 33-38 © 206 Lippincott Williams & Wilkins.

D.A. McQueen, M.D. et al., "Knee Arthrodesis with the Wichita Fusion Nail", Clinical Orthopaedics and Related Research, No. 446, pp. 132-139, © 2006 Lippincott Williams & Wilkins.

D.Grob et al., Translaminar screw fixation in the lumbar spine: technique, indications, results, Eur Spine J (1998) vol. 7:178-186, © Springer-Verlag 1998.

Hans Trouillier, et al., "A Prospective Morphological Study of Facet Joint Integrity Following Intervertebral Disc Replacement with the CHARITE™ Artificial Disc", Eur Spine J. (2006) vol. 15: 174-182 DOI 10.1007/s00586-005-1010-7, Jul. 2005.

Thomas Tischer, et al., "Detailed Pathological Changes of Human Lumbar Facet joints L1-L5 in Elderly Individuals", Eur Spine J Mar. 2006;15(3):308-15, Epub July, vol. 15, 2005.

Nicola C. Gries, et al., "Early Histologic Changer in Lower Lumbar Discs and Facet joints and their Correlation", Eur Spine J (2000) 9:23-29 © Springer-Verlag 2000, Feb. 2000.

Anil Sethi, et al., "Transforaminal Lumbar Interbody Fusion Using Unilateral Pedicle Screws and a Translaminar Screw", Eur Spine J (2009) 18:430-434 DOI 10.1007/s00586-008-0825-4, Mar. 2009.

Sung-Min Kim, M.D., et al., "A Biomechanical Comparison of Supplementary Posterior Translaminar Facet and Transfacetopedicular Screw Fixation after Anterior Lumbar Interbody Fusiion", J Neurosurg (Spine 1) 1:101-107, Jul. 2004.

Jee-Soo Jang, M.D., et. al., "Clinical Analysis of Percutaneous Facet Screw Fixation after Anterior Lumbar Interbody Fusion", J Neurosurg: Spine 3:40-46, Jul. 2005.

Jee-Soo Jang, M.D., et. al., "Minimally Invasive Transforaminal Lumbar Interbody Fusion with Ipsilateral Pedicle Screw and Contralateral Facet Screw Fixation", J Neurosurg: Spine 3:218-223, Sep. 2005.

Natalie M. Best, et al., "Efficacy of Translaminar Facet Screw Fixation in Circumferential Interbody Fusions As Compared to Pedicle Screw Fixation", J Spinal Disord Tech, vol. 19, No. 2, Apr. 2006.

John W. Klekamp, et. al., "Cervical Transfacet Versus Lateral Mass Screws: A Biomechanical Comparison", Journal of Spinal Disorders, vol. 13, No. 6, pp. 515-518, 2000, Lippincott Williams & Wilkins, Inc., Philadelphia: Dec. 2000.

Harri Pihajamäki, et al., "Tissue Response to Polyglycolide, Polydioxanone, Polylevolactide, and Metallic Pins in Cancellous Bone: An Experimental Study on Rabbits", Journal of Orthopaedic Research, Aug. 2006.

Youn-Kwan Park, M.D., "Facet Fusion in the Lumbosacral Spine: A 2-year Follow-Up Study", vol. 51, No. 1, Jul. 2002.

Albert C. Schmidt, M.D., et al., "Lumbar Fusion Using Facet Inlay Grafts", Southern Medical Journal, vol. 68, No. 2., Feb. 1975.

Philipp Schleicher, M.D., et al., "Biomechanical Evaluation of Different Asymmetrical Posterior Stabilization Methods for Minimally Invasive Transforaminal Lumbar Interbody Fusion", J. Neurosurg: Spine, vol. 9, Oct. 2008.

Yasuaki Tokuhashi, M.D., et al., "C1-C2 Intra-articular Screw Fixation for Atlantoaxial Posterior Stabilization", Spine vol. 25, No. 3, pp. 337-241, Lippincott Williams & Wilkins, Inc., Feb. 1, 2000.

Lisa A. Ferrara, et al., "A Biomechanical Comparison of Facet Screw Fixation and Pedicle Screw Fixation", Spine vol. 28, No. 12, pp. 1226-1234, Lippincott Williams & Wilkins, Jun. 15, 2003.

Yukihiro Kai, M.D., et al., "Posterior Lumbar Interbody Fusion Using Local Facet Joint Autograft and Pedicle Screw Fixation", Spine vol. 29, No. 1, pp. 41-46, Lippincott Williams & Wilkins, Inc., Jan. 1, 2004.

Frank M. Phillips, M.D., "Effect of Supplemental Translaminar Facet Screw Fixation on the Stability of Stand-Alone Anterior Lumbar Interbody Fusion Cages Under Physiologic Compressive Preloads", Spine vol. 29, No. 16, pp. 1731-1736, Lippincott Williams & Wilkins, Inc., Aug. 2004.

Akira Igarashi, M.D., et al., "Inflammatory Cytokines Released from the Facet Joint Tissue in Degenerative Lumbar Spinal Disorders", Spine vol. 29, No. 19, pp. 2091-2095, Lippincott Williams & Wilkins, Inc., Oct. 1, 2004.

* cited by examiner

INTRA-FACET FIXATION DEVICE AND METHOD OF USE

RELATED APPLICATIONS

The present application claims priority to U.S. Provisional Patent Application Ser. No. 60/891,616 filed on Feb. 26, 2007, entitled "Facet Fixation and Fusion Screw and Method of Use," the entirety of which is incorporated herein by reference.

FIELD OF THE INVENTION

The present invention relates to methods and devices for spinal stabilization and fusion, and particularly to stabilization of a facet joint.

BACKGROUND OF THE INVENTION

The vertebrae in a patient's spinal column are linked to one another by the intevertebral disc and the facet joints. This three joint complex controls the movement of the vertebrae relative to one another. Each vertebra has a pair of articulating surfaces located on the left side, and a pair of articulating surfaces located on the right side, and each pair includes a superior articular surface and an inferior articular surface. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. In the lumbar spine, for example, one form of treatment to stabilize the spine and to relieve pain involves the fusion of the facet joint.

One known technique for stabilizing and treating the facet joint involves a trans-facet fusion in which pins, screws or bolts penetrate the lamina to fuse the joint. Such a technique has associated with it the risk of further injury to the patient as such translamina facet instrumentation can be difficult to place in such a way that it does not violate the spinal canal and/or contact the dura of the spinal cord or the nerve root ganglia. Further, trans-facet instrumentation has been known to create a rotational distortion, lateral offset, hyper-lordosis, and/or intervertebral foraminal stenosis as the screws tend to compress the facet joint together.

Examples of facet instrumentation currently used to stabilize the lumbar spine include trans-lamina facet screws ("TLFS") and trans-facet pedicle screws ("TFPS"). TLFS and TFPS implants provide reasonable mechanical stability, but, as noted above, they can be difficult to place, have long trajectories, and surgical access can be confounded by local anatomy. In some instances these implants can result in some degree of foraminal stenosis as the screws tend to compress the facet joints together.

Accordingly, there is a need for instrumentation and techniques that facilitate the safe and effective stabilization of facet joints.

SUMMARY OF THE INVENTION

The presently disclosed embodiments provide devices and methods relating to stabilization and/or fusion of a facet joint via intra-facet placement of an implantable interference device (e.g., a post, screw, screw-like device, etc.). The implantable interference device can be adapted to include various configurations for the efficient and safe placement of the device within the facet joint. In general, the device functions as a sort of mechanical key that prevents sliding motion between the diarthroidal surfaces of the facet joint. Additionally, the intra-facet device can be formed of or include a fusion-promoting bioactive material thereby providing a single device and method capable of both fixation and fusion of the facet joint.

In one aspect, the presently disclosed device is an implantable interference device wherein the device is configured to be positioned within a facet joint in an intra-facet configuration. The device can include a conical distal tip, and a shank extending from the distal tip. Optionally, the shank can include a thread running along a length thereof. The diameter of the shank can be configured so as to be substantially constant or variable from the distal to proximal end of the shank. Furthermore, a head can extend from the proximal end of the shank such that the head has a diameter larger than the diameter of the shank thereby preventing over-insertion of the device and/or allowing the head to buttress against portions of opposing facet faces. The head can also be configured to include various protrusions capable of engaging (e.g., cutting into) the opposing faces of the facet joint. In order to facilitate placement of the device within a facet joint, the device can be cannulated thereby allowing for delivery of the device over a guide-wire. Also, the interference device can include exterior and/or interior drive articulations capable of applying a torque along a length of the device.

Additionally, at least a portion of the shank of the interference device can include a fusion-promoting bioactive material formed thereon. For example, the device (or at least a portion of the device) can be formed of the fusion promoting material, the device can include a coating comprising the fusion promoting material, and/or the device can have a "cage-like" configuration wherein the fusion-promoting bioactive material is housed within a non-fusion promoting material. For example, the fusion-promoting material can be cortical allograft bone or a bioceramic-loaded bioabsorbable material (e.g., of Biocryl™ or TriABSorb™).

In another aspect, an implantable interference device is provided which includes a conical distal tip, and a shank (optionally threaded) extending from the distal tip wherein a diameter of the shank undulates from the distal tip to a proximal end of the device. In those embodiments having a thread, the thread can include a configuration such that a major diameter of the shank includes an undulation in the direction from the conical distal tip to a proximal end of the shank. In one aspect, the undulating configuration can be provided by an interference device having a substantially constant minor diameter and an undulating thread height, while in another aspect, the undulating configuration can be formed by an undulating minor diameter of the shank and a substantially constant thread height. Again, these embodiments can include a shank including a fusion-promoting bioactive material. Also, these embodiments can either include or not include a head extending from the proximal end of the shaft of the device.

In another aspect, the presently disclosed embodiments provide a method for facet joint fixation and fusion. The method includes surgically delivering at least one implantable interference device having a shank (optionally threaded) to a facet joint in an intra-facet orientation. Similar to those embodiments described above, the shank can include a proximal end having a head wherein a diameter of the head is larger than a diameter of the shank. Also, in some embodiments, at least a portion of the device can include a fusion-promoting bioactive material. Next, the method includes engaging portions of the shank to opposing faces of the facet joint. The method can further include delivering a first interference device to a first facet joint and a second interference device to a second, corresponding facet joint at the same level of a spine. The first device and the second device can be of the same or different diameters wherein the difference in diameter can allow for a desired distraction of the first and second facet joints. Also, the method can include buttressing opposing faces of the facet joint with the head of the interference device so as to prevent motion of the opposing faces relative to one another. In one embodiment, placement of the device distracts opposing faces of the facet joint to relieve stenosis. As an added advantage, the method can allow for the device(s) to be placed via a minimally invasive surgical procedure.

These and other aspects of the presently disclosed embodiments will be described in detail below.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In general, the presently disclosed embodiments relate to methods for intra-facet spinal fixation and fusion, and to intra-facet fixation device. The fixation and fusion devices disclosed herein are configured for intra-facet delivery to the facet joint. That is, the device is configured to be placed in the plane of the facet joint, between the diarthroidal surfaces of the facet joint and as a mechanical spacer to distract the facet faces and relieve forminal stenosis. As such, the device functions as a sort of mechanical key that prevents sliding motion between the diarthroidal joint surfaces. The intra-facet interference devices disclosed herein also stabilize the joint by distracting the facet faces and placing the joint capsule in tension. Such distraction of the facet face is believed to contribute to alleviating intervertebral foraminal stenosis. Further, intra-facet devices of the type disclosed herein constrain rotational motion at the level of the interference device placement when placed bilaterally.

As will be explained below in detail, the intra-facet device can include a conical distal tip and a shank extending from the distal tip. Optionally, the shank can include a thread extending along a length thereof. The thread (running clockwise or counter-clockwise) can include a substantially uniform, or alternatively, non-uniform major diameter in the direction from a distal end of the shank to a proximal end of the shank. Further, the device can include a head extending from the proximal end of the shank. In one embodiment the head can have a diameter greater than a major diameter of the shank thereby preventing over-insertion of the device into the a facet joint. Also, at least a portion of the shank can include a fusion-promoting bioactive material. As will be shown, the shank (or at least a portion) can be formed of the fusion-promoting bioactive material, the shank can include a coating comprising the bioactive material, and/or the shank can have a "cage-like" configuration capable of at least partially housing the bioactive material. Each of these configurations allows for a single device capable of providing both spinal fixation and fusion.

Figure 1:
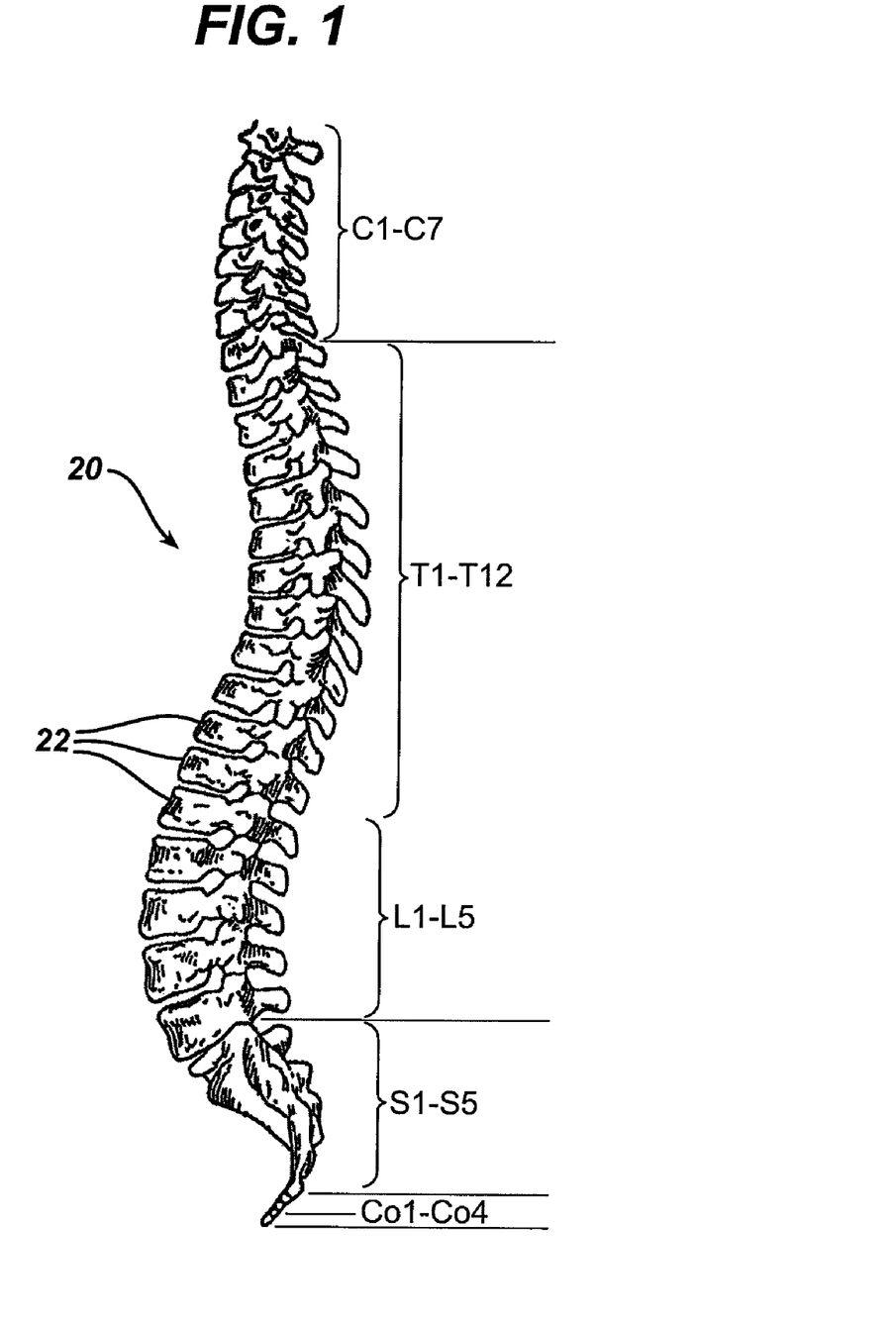
FIG. 1 is a representation of a human spinal column.
Figure 2:
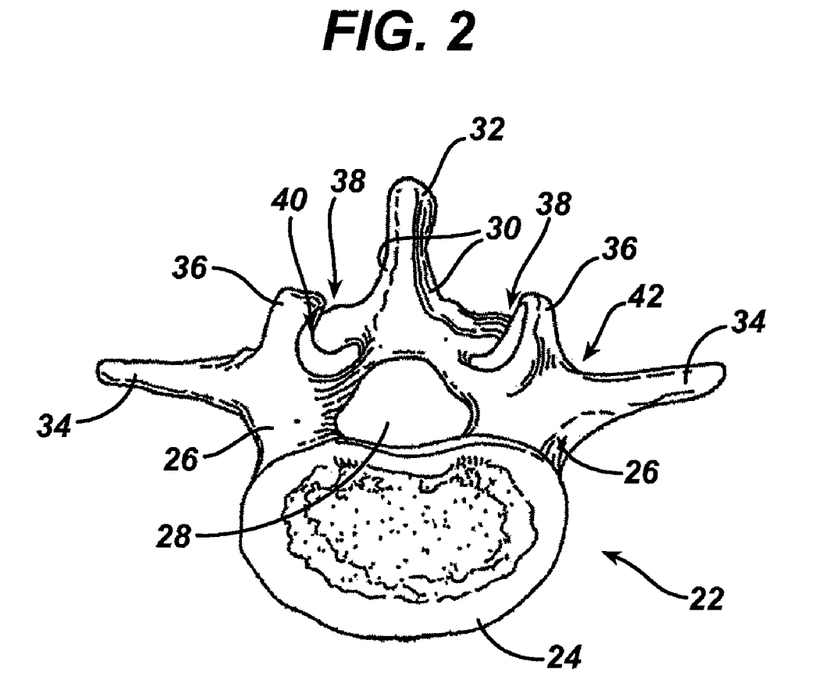
FIG. 2 is a representation of a lumbar vertebrae.
Figure 3:
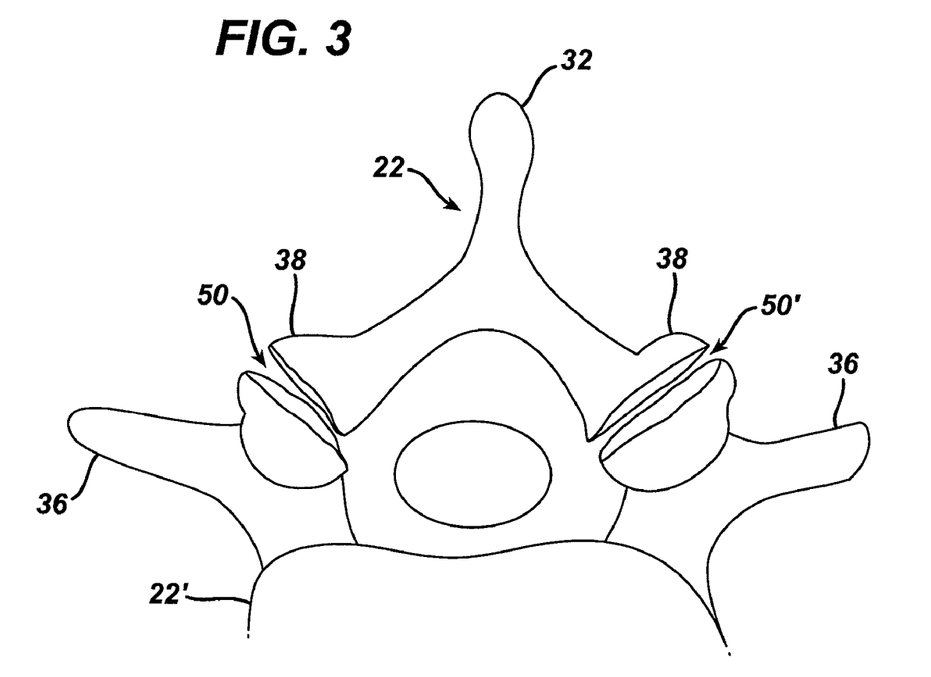
FIG. 3 is a representation of a first facet joint and a corresponding second facet joint formed as a result of a first vertebrae stacked on a second vertebrae.

FIGS. 1-3 provide an overview of the spinal column structure and location of associated facet joints. As FIG. 1 shows, the human spinal column 20 is comprised of a series of thirty-three stacked vertebrae 22 divided into five regions. The cervical region includes seven vertebrae 22, known as C1-C7. The thoracic region includes twelve vertebrae 22, known as T1-T12. The lumbar region contains five vertebrae 22, known as T1-T5. The sacral region is comprised of five vertebrae 22, known as S1-S5. The coccygeal region contains four vertebrae 22, known as Co1-Co4.

FIG. 2 shows a normal human lumbar vertebra 22. Although the lumbar vertebrae 22 vary somewhat according to location, they share many features common to most vertebrae 22. Each vertebra 22 includes a vertebral body 24. Two short bones, the pedicles 26, extend posteriorly from each side of the vertebral body 24 to form a vertebral arch 28. At the posterior end of each pedicle 26 the vertebral arch 28 flares out into broad plates of bone known as the laminae 30. The laminae 30 fuse with each other to form a spinous process 32, to which muscle and ligaments attach. A smooth transition from the pedicles 26 into the laminae 30 is interrupted by the formation of a series of processes.

Two transverse processes 34 thrust out laterally on each side from the junction of the pedicle 26 with the lamina 30. The transverse processes 34 serve as levers for the attachment of muscles to the vertebrae 22. Four articular processes, two superior 36 and two inferior 38, also rise from the junctions of the pedicles 26 and the laminae 30. The superior articular processes 36 are sharp oval plates of bone rising upward on each side from the union of the pedicle 26 with the lamina 30. The inferior processes 38 are oval plates of bone that jut downward on each side. The superior and inferior articular processes 36 and 38 each have a natural bony structure known as a facet. The joint formed by two opposing facets is called the zygapophyseal joint. The superior articular facet 40 faces upward, while the inferior articular facet 42 faces downward. As shown in FIG. 3, when adjacent vertebrae 22, 22' are aligned (i.e., stacked), the facets interlock to form corresponding facet joints 50, 50' positioned at the same level of the spine.

Figure 4A:
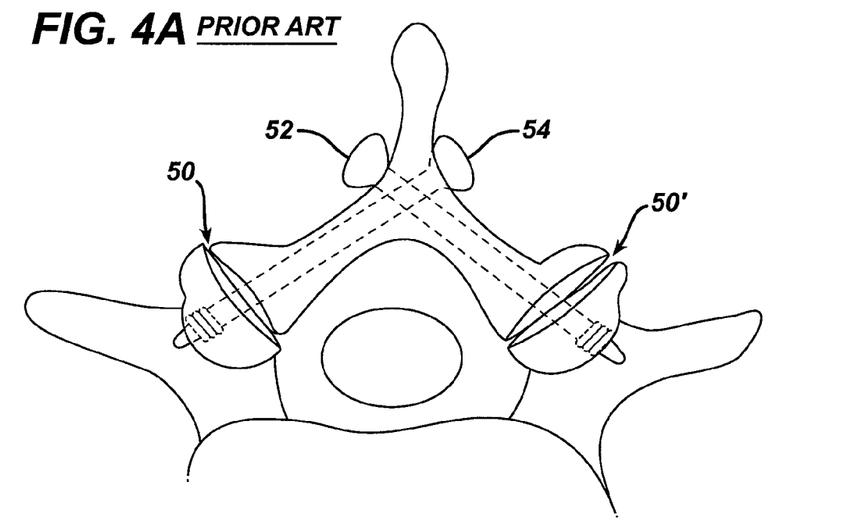
FIG. 4A is a representation of prior art trans-facet placement of fixation screws.
Figure 4B:
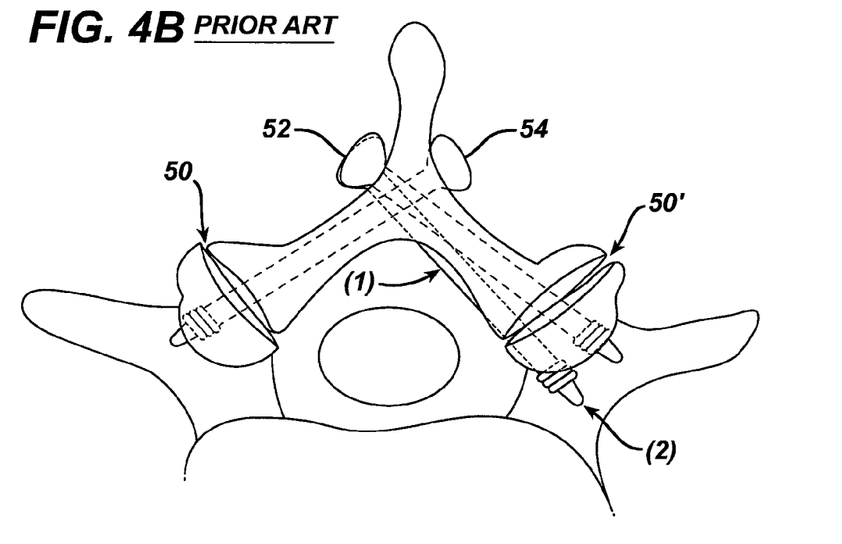
FIG. 4B is a representation of prior art trans-facet delivery of fixation screws wherein one of the trans-facet screws has impinged the spinal column.
Figure 4C:
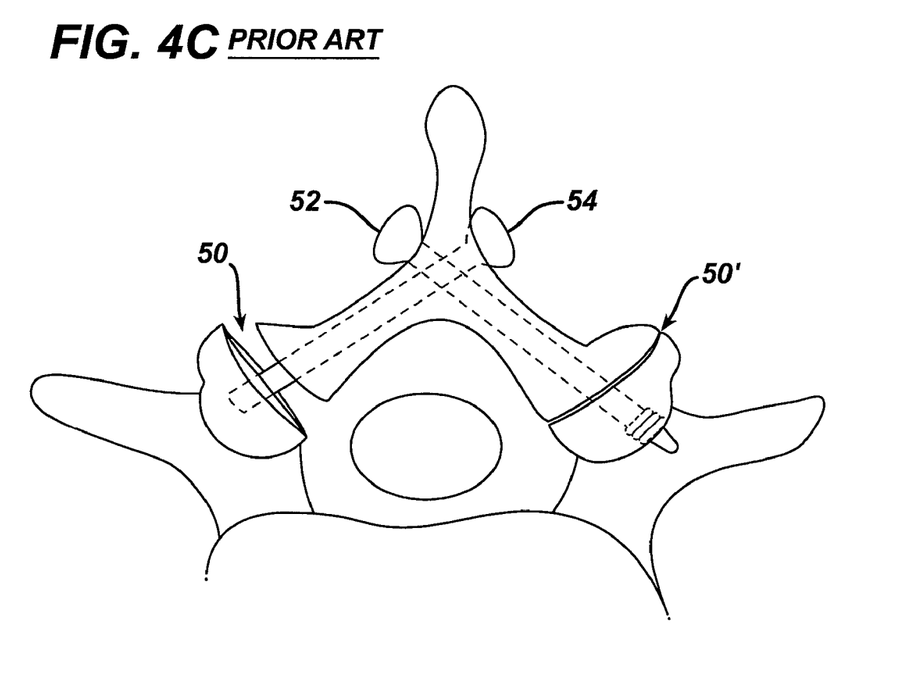
FIG. 4C is a representation of prior art trans-facet delivery of fixation screw wherein incorrect placement of the translaminar screws results in rotational distortion of the joint.

Looking in more detail at FIG. 3, the spinous process 32 and inferior articular processes 38 of the top vertebrae 22 are positioned adjacent to the superior articular processes 36 of the bottom vertebrae 22' and form facet joints 50, 50'. As shown in FIG. 4A, prior art trans-facet fixation procedure includes the insertion of trans-facet screws 52, 54 through bone and across the facet joints 50, 50'. However, such a procedure has been known to result in various problems. For example, FIG. 4B shows that a minor miscalculation in screw placement can result in a trans-facet screw 52 impinging upon the spinal column (as indicated by (1)) and/or impinging upon surrounding nerves (as indicated by (2)), thereby resulting in patient injury. Additionally, trans-facet screw placement procedures can result in unwanted and/or unpredictable rotational distortion (or lateral offset) of the facet joint because of the difficulty of approximating the final position of the trans-facet screws 52, 54 in these procedures. As shown in FIG. 4C, trans-facet placement of the screws 52, 54 can result in significantly different gap sizes in corresponding facet joints 50, 50', thereby resulting in unwanted tension on the spine and ultimately injury to the patient.

Figure 5A:
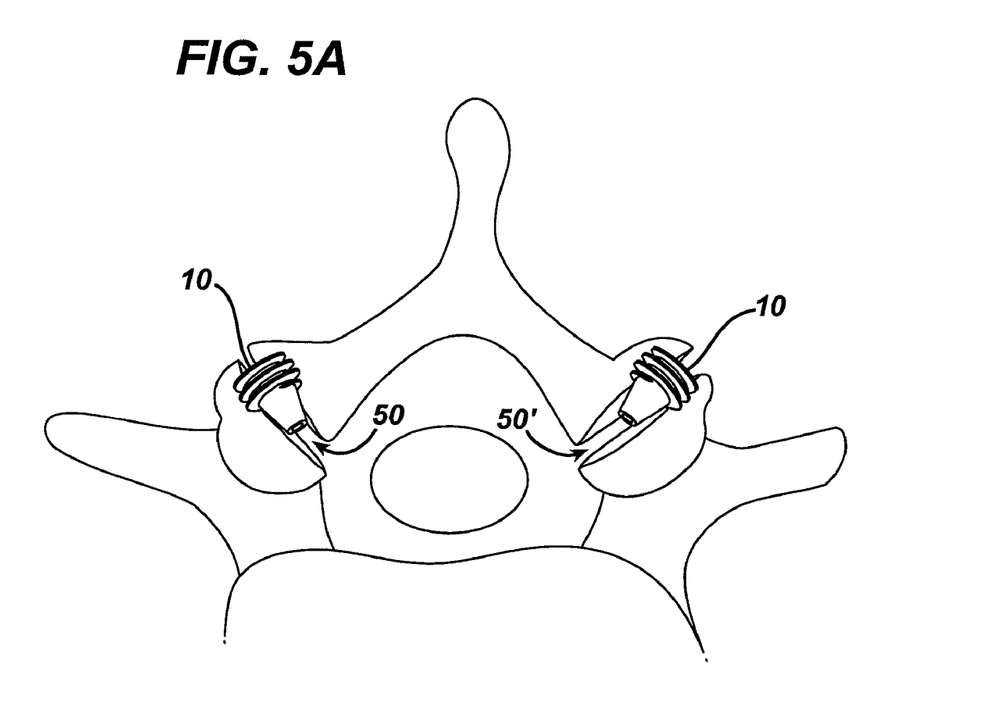
FIG. 5A is a representation of an embodiment of first and second intra-facet impantable interference devices being placed in an intra-facet orientation within corresponding facet joints.

In contrast to trans-facet screw placement techniques, the impantable interference devices disclosed herein are configured to allow for intra-facet placement of the device within the joint. FIG. 5A is an illustrative representation of fusion and fixation devices 10, 10' positioned within corresponding facet joints 50, 50' at the same level of the spine in an intra-facet orientation. In other embodiments, the fusion and fixation devices 10, 10' can be of such a length as to span substantially the entire facet, and/or be of such a length to embed in the corresponding pedicles. As will be appreciated by those skilled in the art, a device of any such length (as will be further discussed below) is within the spirit and scope of the present invention.

As shown, the intra-facet placement eliminates the need to pass the device 10 through bone, but rather allows for delivery (in a minimally invasive manner, for example) along the plane (i.e., in an intra-facet orientation) of the facet joint 50, 50' such that the device 10 engages and is positioned between the opposed superior and inferior faces of the facet joint. As represented in FIG. 5A, an intra-facet device 10 can be delivered bilaterally to both a first facet joint 50 and adjacent, second 50' facet joint at the same level of the spine.

Figure 5B:
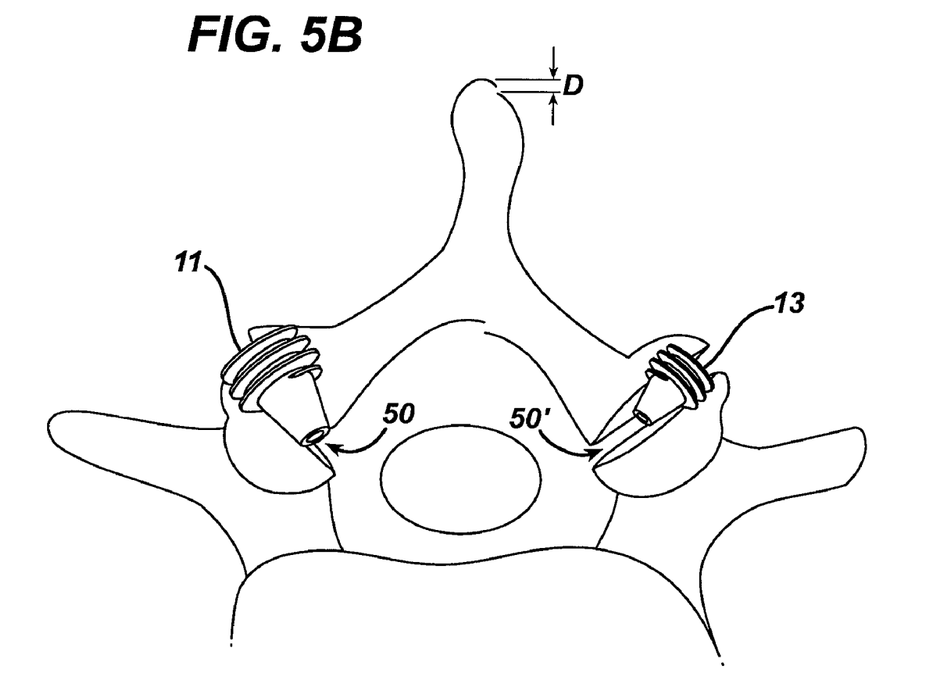
FIG. 5B is a representation of an embodiment of different size intra-facet devices being placed in an intra-facet orientation within corresponding facet joints thereby allowing for a desired distraction of the facet joints.

In one embodiment, intra-facet devices of different dimensions can be delivered to adjacent facet joints at the same level of the spine to provide any desired differential distraction of the facet joint. For example, FIG. 5B illustrates an embodiment of an oversized facet device 11 positioned in a first facet joint 50 while a second, undersized facet device 13 is positioned in an adjacent facet joint 50' to provide the desired distraction (as indicated by 'D' in FIG. 5B).

Such intra-facet delivery provides physicians with a safe and efficient alternative to common trans-facet screw placement procedures. The selection of a suitable fixation device is simplified in that an intra-facet device that is not appropriately sized (e.g., too big, too small) can be easily removed and replaced with an alternative fixation device. Such a removal procedure can be effected by removing the interference device from the plane of the facet joint as opposed to drilling a second passageway through bone (as would be required in trans-facet delivery). Further, intra-facet delivery requires less instrumentation (e.g., device to drill bone) as compared to trans-facet stabilization procedures, thereby reducing the likelihood of contamination and/or infection resulting from the procedure. Furthermore, the simple nature of the intra-facet procedure results in significantly less trauma to the patient.

As an added benefit, the intra-facet devices and procedures disclosed herein are particularly well suited for minimally invasive surgery. That is, the devices can be placed in an intra-facet orientation using one or more small, percutaneous incisions, with or without the need for an access port. Such procedures, which are generally well known to those skilled in the art, tend to result in less operative trauma for the patient than a more invasive procedures. Minimally invasive procedures also tend to be less expensive, reduce hospitalization time, causes less pain and scarring, speed recovery, and reduce the incidence of post-surgical complications, such as adhesions.

Accordingly, the intra-facet device placement techniques, as disclosed herein, provide an efficient and safe alternative to trans-facet spinal fixation. Exemplary interference devices useful for such intra-facet placement techniques are provided below.

Figure 6A:
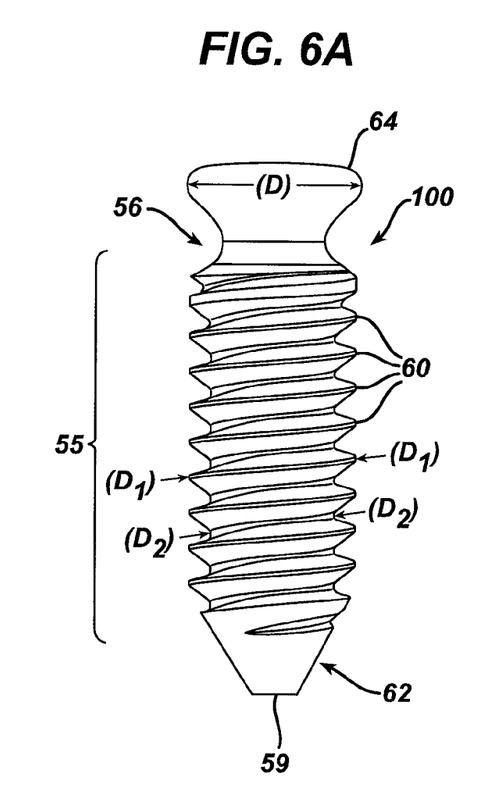
FIG. 6A is a front view of an exemplary embodiment of a presently disclosed intra-facet fixation device.
Figure 6B:
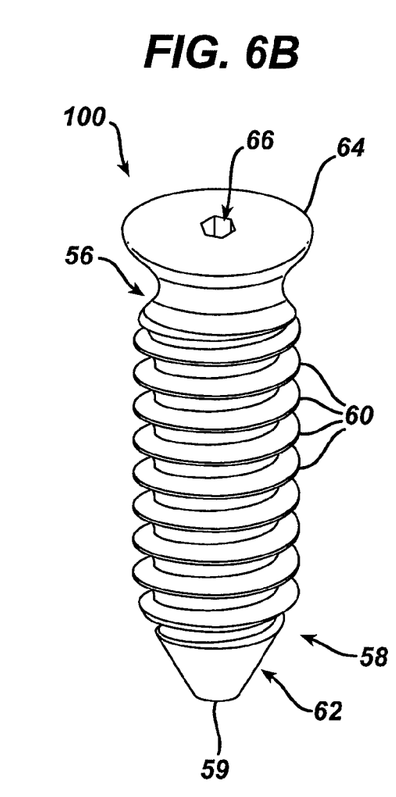
FIG. 6B is a perspective view of the embodiment of FIG. 6A.
Figure 6C:
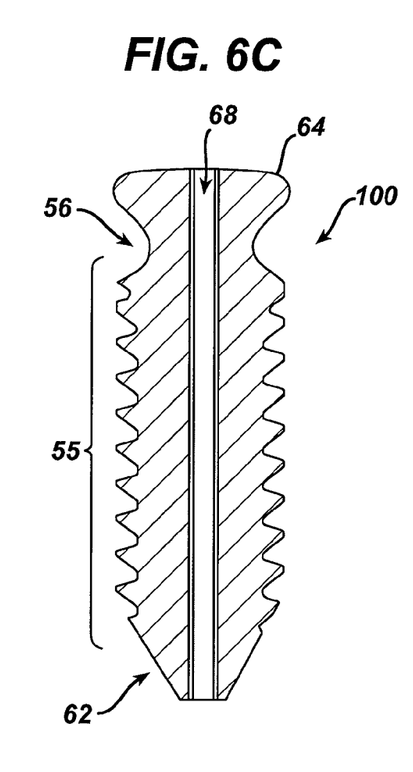
FIG. 6C is a cross-sectional view of the embodiment of FIG. 6A showing an inner lumen sized to accept a guide-wire.

The intra-facet fixation devices provided herein can be configured as any type of intra-facet shank, post, barrel, beam, etc. which can also include any type of fixation mechanism (e.g., threads, an expansion bolt, a deep suture anchor, etc.). In fact, the devices can be configured in virtually any such manner capable of providing the above-described intra-facet fixation. In an exemplary embodiment, the implantable interference device is configured as a screw or screw-like device. Such an embodiment is shown in FIGS. 6A-6C wherein the screw 100 includes a shank 55 having proximal 56 and distal ends 58. A portion of the distal end 58 can be include a conical tip 62 capable of facilitating placement of the screw 100 within the facet joint in an intra-facet orientation. In one embodiment, the distal tip 59 can include a blunt surface. In an alternative embodiment, the distal tip 59 includes a sharp point (not shown). For example, if the screw is cannulated, the distal tip 59 is generally blunt. However, when the cannulation is off-axis, the cannulated screw can include a sharp distal tip. Any such configuration is within the spirit and scope of the present invention. In an exemplary embodiment, the length of the screw is selected to facilitate placement in the facet joint in an intra-facet configuration.

The proximal end 56 of the screw 100 can be adapted so as to prevent over-insertion of the screw 100 thereby substantially preventing injury resulting from penetration of the screw 100 into the spinal column. As will be apparent to one skilled in the art, the proximal end 56 can be adapted in various ways to prevent such over-insertion. For example, as shown in FIGS. 6A-6C, the proximal end 56 can include a head 64 extending from the proximal end of the shank, the head 64 having a diameter (D) greater than a major diameter ($D_1$) of the shank. Those skilled in the art will appreciate that various head designs (e.g., circular, square, oval, X-shaped, etc.) capable of preventing over-insertion are within the spirit and scope of the present invention. The head 64 can be a distinct element (e.g., anchored to the device by some attachment means) or can be integral with the screw 10 (e.g., a screw head). In fact, the head can be any virtually any platter-shaped element that is configured to span the facet faces and substantially prevent facet slippage, translation, and any other normal facet motion. The head can also be configured to act as a buttress against the opposing facets thereby adding stability to the joint.

Figure 7A:
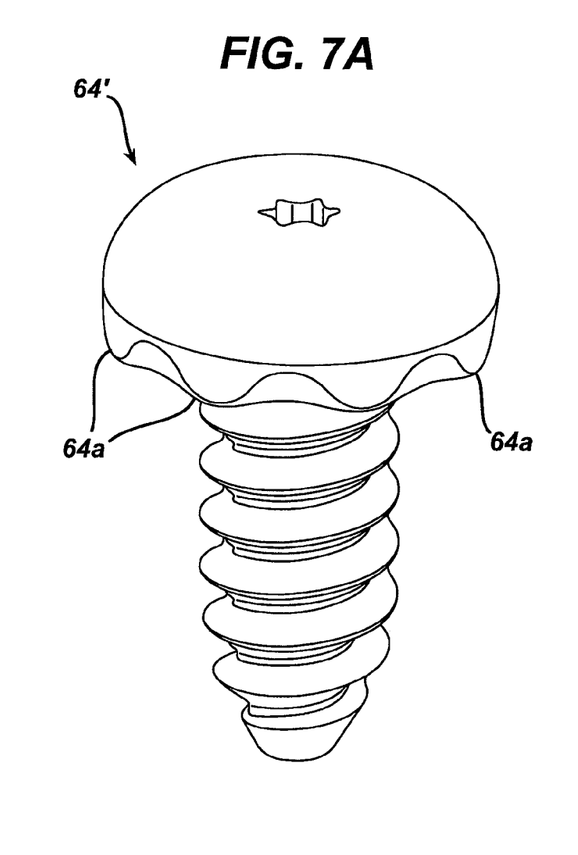
FIG. 7A is a front view of an alternative embodiment of a head formed at a proximal end of an embodiment of the device.
Figure 7B:
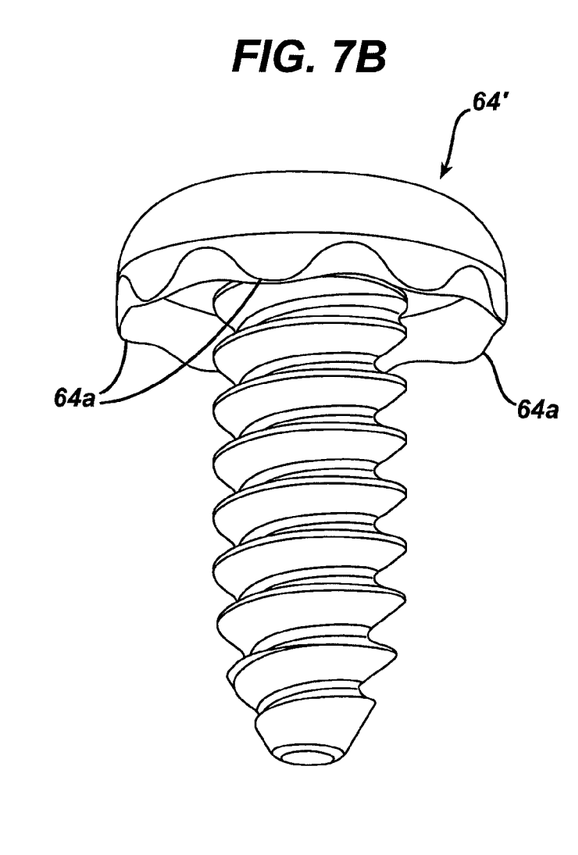
FIG. 7B is a perspective view of the embodiment of FIG. 7A.

Additionally, the head can be adapted to include a plurality of surface features (e.g., protrusions) that are capable of engaging (e.g., cutting into or piercing) opposing faces of the facet joint. Such protrusions enhance the ability of the head to stabilize the device within the joint, and further assist in preventing over-insertion and/or rotation of the screw 100. As shown in FIGS. 7A-7B, the screw head 64' can include a bottle-cap configuration wherein the head 64' includes a series of protrusions 64a capable of cutting into bone so as to facilitate stabilization of the screw within the facet joint, and further to help prevent over-insertion of the screw. Those skilled will appreciate that heads having various shapes, sizes, and/or orientations of bone-penetrating protrusions are within the spirit and scope of the present invention.

As further shown in FIGS. 6A-6C, the shank 55 can have a thread 60 formed thereon with a configuration such that a major diameter ($D_1$) and a minor diameter ($D_2$) of the thread 60 can remain substantially uniform in the direction from the distal conical tip 62 to the proximal end 56 of the shank 55. In another embodiment (not shown), the major diameter of the screw 100 can increase from the distal 58 to proximal end 56 of the shank 55. The thread 60 can be continuous or non-continuous. In the exemplary embodiment of FIGS. 6A-6C, the thread 60 begins proximal to the distal tip 59 and proceeds along substantially the entire length of the shank 55, terminating before the head 64. In an alternative embodiment, the thread 60 can extend along the entire distal end 58. One skilled in the art will appreciate that the thread 60 can be configured to run clockwise or counter-clockwise. The use of clockwise and counter-clockwise threads facilitates bi-lateral placement of such screws. For example, if the threads of both intra-facet screws run in the same direction, there is potential for the superior vertebral body to be shifted in the direction of the thread rotation (i.e., if both screws had clockwise threads, the superior vertebral body would tend to shift to the right during screw placement).

The threads can include various sizes and/or dimensions. In an exemplary embodiment, the threads have a buttress cross-section, and a substantially constant thread crest height, thickness, and pitch along the length of the screw. In one embodiment, the root diameter of the screw can be proportional to the facet distraction distance after screw placement within the joint. Further, the thread depth relates to bony purchase and correlates to screw extraction strength. Such features can be optimized for stabilization of the facet joint via placement of the screw within the facet joint in an intra-facet configuration.

Various dimensions of the screw are within the spirit and scope of the present invention. For example, the screw can have a length in the range of about 25 mm to about 30 mm, a major diameter in the range of about 6 mm to about 10 mm, and a minor diameter in the range of about 4 mm to about 8 mm. Additionally, the distance between adjacent thread heights can be in the range of about 1 mm to about 3 mm. Those skilled in the art will appreciate that various screw dimensions are within the spirit and scope of the present invention.

Referring to FIG. 6B, the proximal facing surface of the screw head 64 can include a feature 66 capable of receiving a driver instrument (e.g., a screwdriver) for delivery of the screw 100 to the facet joint. The feature 66 can be of any suitable design as is known in the art. For example, the feature 66 can be an internal drive feature, such as a hex-shaped socket, capable of seating a complementary male drive feature of a driver tool. Similarly, the feature 66 can be a male feature (not shown) capable of mating with a complementary female drive feature of a driver tool. Regardless of the shape or configuration of the feature 66, it should be effective to enable application of a torque along the entire shaft of the screw 10 using a suitable driver tool.

As shown in FIG. 6C, the screw 10 can be a cannulated screw that includes an inner lumen 68 that extends along its entire length. The lumen can be of any suitable diameter, but in one embodiment it is capable of receiving a Kirschner wire ("K-wire"), which can serve as a guide-wire for delivery of the cannulated screw 10 to the facet joint.

Various alternative embodiments can include an interference device having an undulating configuration in which the major diameter ($D_1$) of the shank varies along the length of the device. Such an undulating configuration can provide stress relief and/or focus an absorbed force to a specific location of the device to enhance the ability of the interference device to support such a loading force. For example, the undulations can provide flexibility to the device such as by thickening the minor diameter's cross section resulting in more bending strength or can provide an intentional fracture zone thereby providing stress relief. An undulating configuration can be formed in a number of ways, including by maintaining a substantially constant minor diameter ($D_2$) of the shank while providing an undulating thread height along the length of the device, or by maintaining a substantially constant thread height, but varying the minor diameter (D2) along the length of the device. These embodiments are further described below.

Figure 8A:
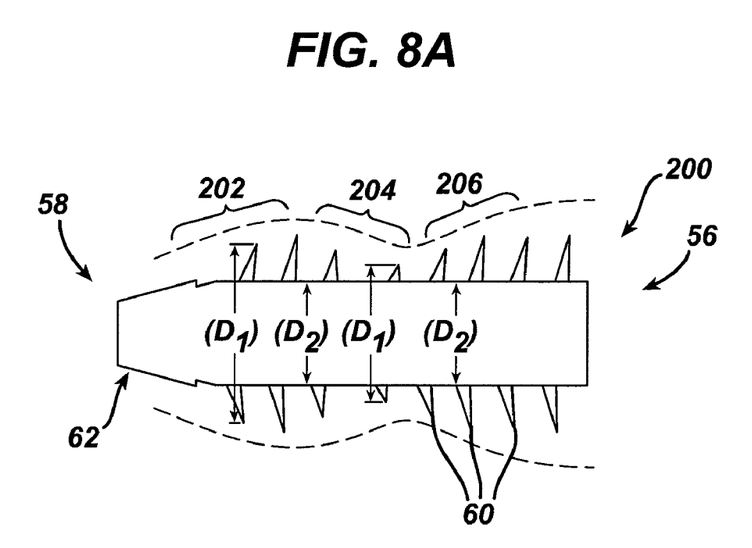
FIG. 8A is a cross-sectional view of an alternative embodiment of an undulating intra-facet fixation device.

FIG. 8A shows one example of an implantable interference screw 200 having an undulating configuration. In this embodiment, the minor diameter ($D_2$) of the screw 200 remains substantially constant throughout its length and the undulation is achieved by varying the height of the threads 60. That is, the major diameter ($D_1$) of the screw 200 varies. In such embodiments, the screw can either include or not include a head extending from the proximal end of the shank. As shown in FIG. 8A, the screw 200 has a first region of increasing major diameter 202, a first region of decreasing major diameter 204, and a second region of increasing diameter 206, and so on. One skilled in the art will appreciate the number and size of the regions of increasing and decreasing major diameter can vary depending on factors such as patient size and condition, and the length of the screw.

Figure 8B:
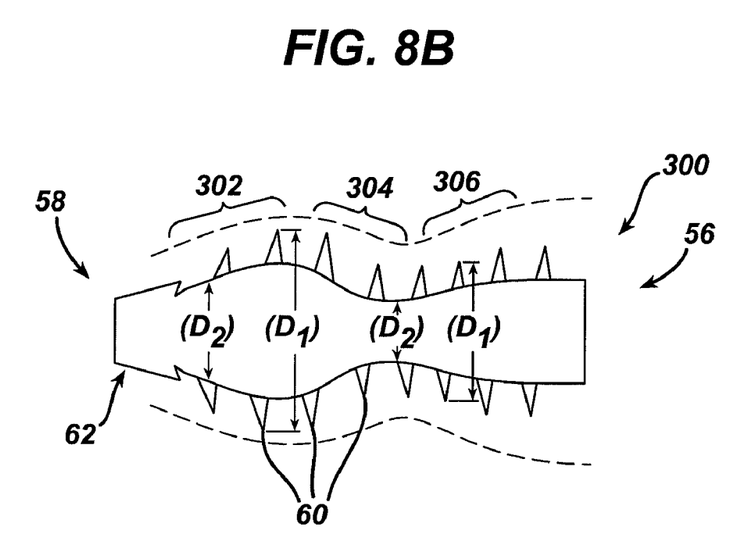
FIG. 8B is a cross-sectional of another alternative embodiment of an undulating intra-facet fixation device.

FIG. 8B shows another example of an intra-facet screw 300 having an undulating configuration. In this embodiment, minor diameter ($D_2$) of the screw 300 undulates throughout its length and the undulation is achieved by maintaining a substantially constant height of the threads 60. That is, once again, the major diameter ($D_1$) of the screw 300 varies. As shown in FIG. 8B, the screw 300 has a first region of increasing major diameter 302, a first region of decreasing major diameter 304, and a second region of increasing diameter 306, and so on.

In addition to the various features discussed above, the intra-facet devices provided herein can be configured to allow for spinal fusion as well as spinal fixation. Any of the embodiments disclosed herein can include or be formed of a fusion-promoting bioactive material so that the intra-facet device actively participates in spinal fusion. In an exemplary embodiment, the intra-facet device is formed from the bioactive material. In another embodiment, a bioactive material can be formed as a coating on a non-bioactive material from which the intra-facet device is formed. For example, the intra-facet device can be formed of a metal and be coated with a fusion-promoting bioactive material. In an alternative embodiment, the non-fusion promoting material (e.g., metal) can form a "cage-like" device capable of housing and releasing the fusion-promoting material. A benefit of these embodiments is the added stability provided by the non-fusion material.

The fusion-promoting bioactive material being any material capable of actively participating in fusion. For example, a suitable fusion-promoting bioactive material from which to form the entire intra-facet device can be any type of allograft bone material. In an exemplary embodiment, the bioactive material can be allograft bone material (such as Allowashed™ available from LifeNet, Inc.; Virginia Beach, Va.). In another example, the material can be a bioresorbable plastic (poly-lactic acid, polyglycolic acid, their derivatives and/or blends), poly-anhydride (PolymerDrug™ by PolyMerix, Piscataway, N.J.), polymerized sugars or starches (Eureka™ by Surmodics of Eden Prairie, Minn.), bioceramic (HIP Vitox™ alumina or Zyranox™ zirconia by Morgan Advanced Ceramics of Fairfield, N.J.; crystalline hydroxyapatite, tricalcium phosphates or combinations of these materials by Berkeley Advanced Biomaterials of San Leandro, Calif.), bioceramic-loaded bioabsorbable material, or dense protein (Novasilk™ by Protein Polymer Technologies of San Diego, Calif.). Exemplary embodiments of such bioabsorbable materials include Biocryl™ (an 85% PLA/PGA, 15% tricalcium phosphate material available from Depuy Mitek, a Johnson & Johnson Company; Raynham, Mass.) or TriAB-Sorb™ (a 5% hydroxyapatite, 95% PLA material available from Depuy Mitek, a Johnson & Johnson Company; Raynham, Mass.) As another example, the material can be an osseointegrating polymer such as PEEK/Optima™ (available from Invibio, Inc.; Greenville, S.C. or from Solvay Advanced Polymers; Augusta, Ga.). Those skilled in the art will appreciate that any combination of these materials are within the spirit and scope of the present invention.

The non-fusion promoting material can be any suitable biocompatible material. For example, the non-fusion promoting material may be a metal or metal alloy. In an exemplary embodiment, the non-fusion promoting material is titanium or a titanium alloy (i.e., Ti 6Al 4V). Those skilled in the art will appreciate that various other such biocompatible materials are within the spirit and scope of the present invention.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable interference device, comprising:
    a conical distal tip;
    a shank extending from the distal tip;
    a unitary head extending from a proximal end of the shank, the head having a diameter greater than a major diameter of the shank; and
    at least one protrusion formed on a distal-facing surface of the head and extending distally therefrom, the at least one protrusion being unitary with the head, the protrusion having a length adapted to engage a face of a facet joint,
    wherein the implantable interference device is configured to engage opposing faces of the facet joint.

2. The device of claim 1, wherein at least a portion of the shank includes a fusion-promoting bioactive material formed thereon.

3. The device of claim 1, wherein a portion of the device is formed of a fusion-promoting bioactive material.

4. The device of claim 1, wherein a thread runs along at least a portion of the shank in one of a clockwise or counter-clockwise direction.

5. The device of claim 1, wherein the device is cannulated, having an inner lumen extending through the device, along a longitudinal axis thereof, from the distal tip to the head.

6. The device of claim 1, wherein the major diameter of the shank is substantially constant along a length of the shank.

7. The device of claim 1, wherein the major diameter of the shank undulates along a length of the shank.

8. An implantable interference device, comprising:
    a conical distal tip; and
    a unitary shank extending from the distal tip such that a major diameter of the shank undulates along a length of the shank from the conical distal tip to a proximal end of the shank; and
    a head extending from the proximal end of the shank, the head having a diameter greater than the diameter of the shank,
    wherein a proximal-most end of the implantable interference device is configured for intra-facet placement within a facet joint.

9. The device of claim 8, wherein the thread is configured such that a major diameter of the shank undulates from the conical distal tip to the proximal end of the shank.

10. The device of claim 9, wherein a minor diameter of the shank undulates in the direction from the conical distal tip to the proximal end of the shank.

11. The device of claim 9, wherein a minor diameter of the shank remains substantially constant from the conical distal tip to the proximal end of the shank.

12. The device of claim 8, wherein at least a portion of the shank includes a fusion-promoting bioactive material formed thereon.

13. A method for facet joint fixation, comprising:
    surgically delivering at least one implantable interference device to a facet joint in an intra-facet orientation, the device having a shank which includes a unitary head formed at a proximal end of the shank, the head having a diameter larger than a major diameter of the shank;
    engaging portions of the shank to opposing faces of the facet joint; and
    piercing bone proximate to the facet joint with at least one protrusion, the at least one protrusion being unitary with the head.

14. The method of claim 13, further comprising delivering a first interference device to a first facet joint and a second interference device to a second, corresponding facet joint at the same level of a spine.

15. The method of claim 14, wherein a diameter of the first interference device is different than the diameter of the second, corresponding interference device, the difference in diameter allowing for a desired distraction of the first and second facet joints.

16. The method of claim 13, wherein the surgically delivering step is conducted in a minimally invasive surgical procedure.

17. The method of claim 13, wherein a portion of the interference device includes a fusion-promoting bioactive material.

18. The method of claim 13, wherein placement of the interference device distracts the opposing faces of the facet joint to relieve stenosis.

19. The method of claim 13, further comprising:
buttressing opposing faces of the facet joint with the head of the interference device so as to prevent motion of the opposing faces relative to one another.

20. The method of claim 13, wherein the at least one protrusion pierces the facet joint.

21. The method of claim 13, wherein the at least one protrusion is formed on a distal facing surface of the unitary head.

* * * * *